United States Patent
Hughes et al.

(10) Patent No.: US 10,144,949 B2
(45) Date of Patent: Dec. 4, 2018

(54) SYSTEMS AND METHODS FOR ELECTROCHEMICAL ASPARTATE TRANSAMINASE (AST) AND ALANINE TRANSAMINASE (ALT) DETECTION AND QUANTIFICATION

(71) Applicant: Polymer Technology Systems, Inc., Indianapolis, IN (US)

(72) Inventors: Gary L. Hughes, Camby, IN (US); Aniruddha Patwardhan, Fishers, IN (US)

(73) Assignee: Polymer Technology Systems, Inc., Indianapolis, IN (US)

(*) Notice: Subject to any disclaimer, the term of this patent is extended or adjusted under 35 U.S.C. 154(b) by 0 days.

(21) Appl. No.: 15/392,593

(22) Filed: Dec. 28, 2016

(65) Prior Publication Data

US 2017/0183711 A1    Jun. 29, 2017

Related U.S. Application Data

(60) Provisional application No. 62/271,753, filed on Dec. 28, 2015.

(51) Int. Cl.
| | | |
|---|---|---|
| C12Q 1/52 | (2006.01) | |
| C12Q 1/00 | (2006.01) | |
| C12N 9/88 | (2006.01) | |
| C12N 9/02 | (2006.01) | |

(52) U.S. Cl.
CPC ............. *C12Q 1/52* (2013.01); *C12N 9/0008* (2013.01); *C12N 9/88* (2013.01); *C12Q 1/005* (2013.01); *C12Y 102/03003* (2013.01); *C12Y 401/01003* (2013.01)

(58) Field of Classification Search
CPC ..................................................... C12Q 1/52
See application file for complete search history.

(56) References Cited

U.S. PATENT DOCUMENTS

| | | |
|---|---|---|
| 2002/0130043 A1 | 9/2002 | Hodges et al. |
| 2005/0015000 A1 | 1/2005 | Djennati et al. |
| 2011/0042211 A1* | 2/2011 | Huang ............... G01N 27/3272 204/403.04 |
| 2011/0318755 A1 | 12/2011 | Piasio et al. |
| 2013/0026050 A1 | 1/2013 | Harding et al. |
| 2013/0216452 A1 | 8/2013 | Phan et al. |

OTHER PUBLICATIONS

Paraiso et al. Int J Electrochem Sci., 2014, 9:1286-1297.*
Guerci et al. Diabetes Care, 2003, 26:1137-1141.*
(Han, YD et al.) Multienzyme-modified biosensing surface for the electrochemical analysis of aspartate transaminase and alanine transaminase in human plasma. Analytical and Bioanalytical Chemistry. 2011; vol. 400; abstract; p. 798, col. 1, 2nd-3rd paragraphs; scheme 1; p. 799, col. 1, 1st paragraph; col. 2, 1st-2nd paragraphs; p. 800, col. 1, 2nd paragraph; p. 801, col. 1, 2nd paragraph; col. 2, 1st-3rd paragraphs.
(Mizutani, F et al.) Amperometric determination of pyruvate, phosphate and urea using enzyme electrodes based on pyruvate oxidase-containing poly (vinyl alcohol)/polyion complex-bilayer membrane. Electrochimica Acta. 2000. vol. 45; abstract; p. 2947, col. 2, 2nd paragraph; p. 2949, col. 2, 3rd-4th paragraphs.

* cited by examiner

*Primary Examiner* — Bin Shen
(74) *Attorney, Agent, or Firm* — Woodard, Emhardt, Moriarty, McNett & Henry LLP

(57) ABSTRACT

A system for electrochemically detecting AST and ALT includes a first sampler for producing pyruvate from ALT and a second sampler for producing pyruvate from AST. The system further includes an electrochemical test strip for receiving processed samples from the first and second samplers, the processed samples containing pyruvate. The system further includes a meter for reading the electrochemical test strip and indicating an amount of AST and ALT in the sample.

5 Claims, 5 Drawing Sheets

SYSTEMS AND METHODS FOR ELECTROCHEMICAL ASPARTATE TRANSAMINASE (AST) AND ALANINE TRANSAMINASE (ALT) DETECTION AND QUANTIFICATION

CROSS REFERENCE TO RELATED APPLICATION

This application claims the benefit of U.S. Provisional Patent Application 62/271,753 filed Dec. 28, 2015, and hereby incorporated by reference to the same extent as though fully disclosed herein.

BACKGROUND

The AST/ALT ratio is the ratio between the concentrations of the enzymes aspartate transaminase (AST) and alanine transaminase (ALT). Generally, AST and ALT relate to the health of an individual's liver. These enzymes are found in the blood of individuals. If the AST measurement is lower than the ALT measurement, it is generally suggestive of some sort of liver disease, especially those caused by alcohol. Hepatitis C or other liver diseases may also result in an imbalance in the levels of AST and ALT. It is desirable to have a point-of-care test to test for these analytes.

BRIEF SUMMARY

In one embodiment, a system for electrochemically detecting AST includes a sampler for producing pyruvate from AST; an electrochemical test strip for receiving a processed sample from the sampler, the processed sample containing pyruvate; and a meter for reading the electrochemical test strip and indicating an amount of AST in the sample. In one configuration, the sampler contains L-Alanine+alpha-Ketoglutarate. In another configuration, the electrochemical test strip includes phosphate and ferricyanide. Optionally, the electrochemical test strip further includes pyruvate oxidase. In one alternative, the sampler includes a heating element. In another alternative, the sampler includes a timer. Alternatively, the meter includes a timer.

In one embodiment, a system for electrochemically detecting ALT includes a sampler for producing pyruvate from ALT; an electrochemical test strip for receiving a processed sample from the sampler, the processed sample containing pyruvate; and a meter for reading the electrochemical test strip and indicating an amount of ALT in the sample. In one configuration, the sampler contains L-Aspartic acid+alpha-Ketoglutarate. In another configuration, the sampler further contains oxaloacetate decarboxylase. Optionally, the electrochemical test strip includes phosphate and ferricyanide. Alternatively, the electrochemical test strip further includes pyruvate oxidase. In one configuration, the sampler includes a heating element. Optionally, the sampler includes a timer. Alternatively, the meter includes a timer. In another configuration, the electrochemical test strip contains a heating element to heat the sample using the meter as a source of energy.

In one embodiment, a system for electrochemically detecting AST and ALT includes a first sampler for producing pyruvate from AST and a second sampler for producing pyruvate from ALT. The system further includes an electrochemical test strip for receiving processed samples from the first and second samplers, the processed samples containing pyruvate. The system further includes a meter for reading the electrochemical test strip and indicating an amount of AST and ALT in the sample. Optionally, the first sampler contains L-Alanine+alpha-Ketoglutarate. Alternatively, the second sampler contains L-Aspartic acid+alpha-Ketoglutarate. In one configuration, the second sampler further contains oxaloacetate decarboxylase. In one configuration, the electrochemical test strip further contains oxaloacetate decarboxylase. In another configuration, the electrochemical test strip includes phosphate, pyruvate oxidase, and ferricyanide.

In one embodiment, a system for electrochemically detecting phosphate includes an electrochemical test strip for receiving a sample; the electrochemical test strip includes pyruvate, pyruvate oxidase, and ferricyanide; and a meter for reading the electrochemical test strip and indicating an amount of phosphate in the sample.

DETAILED DESCRIPTION

Figure 1:
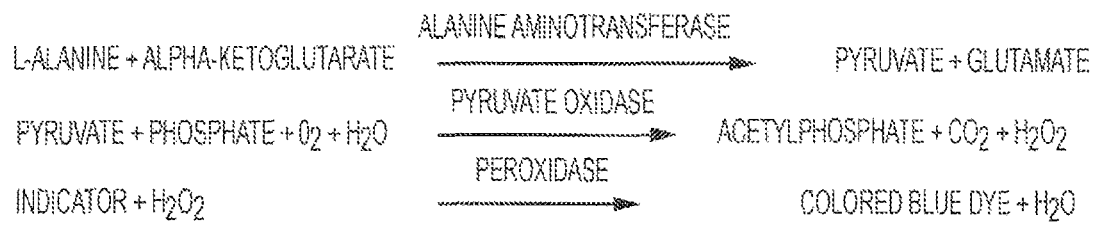
FIG. 1 shows the standard point-of-care colorimetric ALT reaction.

Certain terminology is used herein for convenience only and is not to be taken as a limitation on the embodiments of the systems and methods for electrochemical aspartate transaminase (AST) and alanine transaminase (ALT) detection and quantification. In the drawings, the same reference letters are employed for designating the same elements throughout the several figures.

Disclosed are embodiments of ALT and AST assays. One of the challenges of colormetric assays has been the temperamental nature of chromogens on membranes. It is necessary to have a highly sensitive chromophore in order to test for ALT or AST. Some challenges with chromophores are fading during the reaction, instability in the compounding process, light sensitivity, insolubility, and limited by pH ranges. One method and system for overcoming these shortcomings is that these assays could be developed using electrochemistry. By going to an electrochemical assay, it eliminates any need for a chromophore. Some advantages include:

1. By having an amperometric ALT and AST assay, no membranes are necessary. This provides for a cheaper manufacturing process and avoids being at the mercy of membrane manufacturers' ability to produce reliable, consistent product.
2. Calibration of the analyzer is easier with electrochemical testing. Measuring current (nA) is a standardized process, whereas standardizing reflectance is more difficult.
3. Because the ALT and AST assays are measuring enzymes, the time of testing is longer than most assays. This becomes problematic for colorimetric tests because many chromophores display fading over time, particularly in a heated environment. By testing ALT and AST in an electrochemical environment, there is no need for a chromophore.

4. Electrochemical test strips generally are inexpensive to produce due to the automation and small amounts of reagent used.
5. Testing ALT and AST via electrochemistry probably will result in better precision.
6. In many embodiments, the test range of ALT and AST could be larger than a reflectance assay. Reflectance assays are limited by the amount of color that is produced, whereas electrochemical assays are not limited by the current produced.
7. In many embodiments, the sample size will be small: ~1.2 µL instead of 15 µL.
8. In many embodiments, there may be no need of a transfer pipette to apply blood to a strip since the blood sample is simply wicked into the sampling port.

Alanine aminotransferase (ALT) and aspartate aminotransferase (AST) are enzymes primarily associated with the liver. AST primarily is found in the liver, heart, and skeletal muscles, while ALT primarily is found in the liver. The release of ALT and AST from liver cells to the blood stream is an indication of hepatic cell damage or death. There are various medical reasons an ALT or AST test would be recommended. In a point-of-care setting, such assays may be used to monitor patients who are taking medications that may cause adverse effects on the liver.

Embodiments described herein provide a novel reaction pathway to conduct an electrochemical ALT and AST assay. Once pyruvate is produced, the reaction is the same for both the ALT and AST reactions. We have discovered through literature searches and empirically that pyruvate oxidase specifically from *E. Coli* will react directly with a mediator that will be reduced at the electrode. This provides for an electrochemical reaction.

Proposed Electrochemical ALT Reaction Pathway:

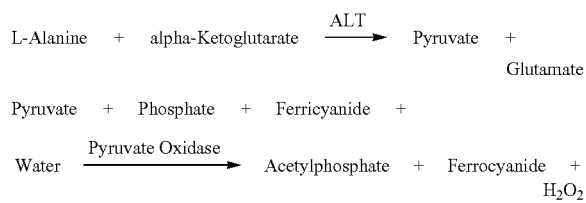

Proposed Electrochemical AST Reaction Pathway:

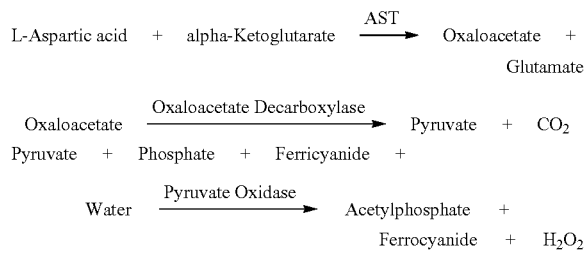

Most ALT/AST reaction pathways that use pyruvate oxidase require the use of oxygen and react the peroxide formed with a chromophore. This process takes an additional reaction step than what is proposed. Furthermore, the journal articles and papers on proposed electrochemical ALT/AST assays also make use of the additional peroxide-peroxidase reaction step. We have shown that we can eliminate this peroxide-peroxidase step by using a pyruvate oxidase from *E. Coli* which reacts directly with the mediator. In theory, by eliminating reaction steps, the precision and speed of the assay should improve.

FIG. 1 shows the standard point-of-care colorimetric ALT reaction. This reaction and the similar AST reaction have significant issues with the sensitivity of membranes and chromophores.

Figure 2:
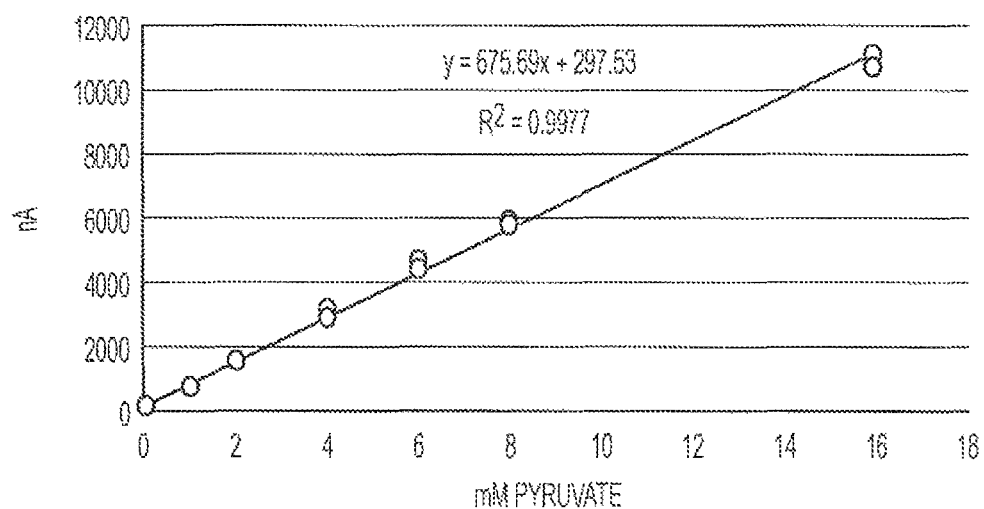
FIG. 2 shows a proof-of-concept graph was conducted without any optimization of reagents.

Proof of concept has been shown for an electrochemical ALT and AST assay by measuring pyruvate amperometrically. FIG. 2 shows a proof-of-concept graph was conducted without any optimization of reagents. Using phosphate, pyruvate oxidase from *E. Coli*, potassium ferricyanide, co-factors, and polymer binder, an electrochemical sensor was made to measure pyruvate. In approximately ten seconds of time, pyruvate was able to be measured amperometrically (see FIG. 2).

By showing an electrochemical pyruvate reaction, it is only a matter of reacting the ALT and AST with their reactants to produce pyruvate. This may be done in a number of different ways. One embodiment would be to have all components reacted on the electrochemical test strip. Another approach may be to involve a sample shaker like a "Redwood sampler" which contains the reactants that will react with the enzymes (ALT or AST) to produce pyruvate. In this embodiment, there is a timer started when the blood was allowed to mix with the reactants. In some embodiments, when the blood is introduced to the reactants, pushing the parts together on the Redwood sampler would start a timer on the sampler. In other embodiments, this time is tracked on the meter by depressing a button or giving another indication to the meter when the sample is added. After the given amount of time, the strip would be dosed by the sampler contents. In some embodiments, inside the sampler, it is possible to create an exothermic reaction by using calcium oxide, sodium acetate, or any such chemicals to add heat to the reaction. By adding heat, the ALT and AST reaction will occur more quickly. Alternatively, the meter may apply heat or an electrical heating element may be included in the sampler. In another configuration, the electrochemical test strip contains a heating element to heat the sample using the meter as a source of energy.

Figure 3A:
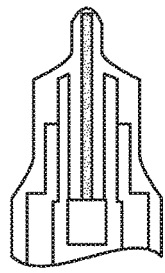
FIGS. 3a-3c show one embodiment of a sample collector (Redwood Sampler) containing reactants for reacting with ALT or AST.
Figure 3B:
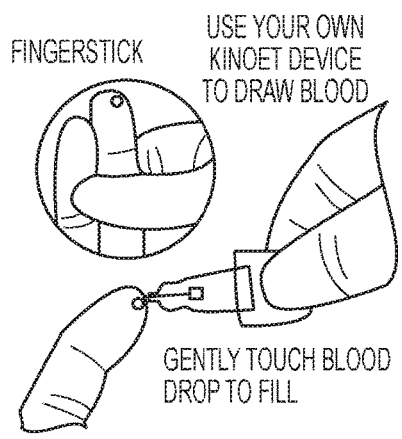
Figure 3C:
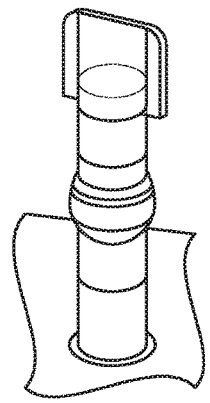

FIGS. 3a-3c show one embodiment of a sample collector (Redwood Sampler) containing reactants for reacting with ALT or AST. In FIG. 3a, a capillary tube system for taking a blood sample is shown. FIG. 3b shows the method of obtaining a blood sample using the capillary tube system. FIG. 3c shows the capillary tube system after it has been inserted in a receiver. This receiver carries the chemicals for the reaction described above. Additionally, the receiver may include a heating element as described, as well as a timer (however, these elements may be located in the capillary tube sampler as well).

Figure 4:
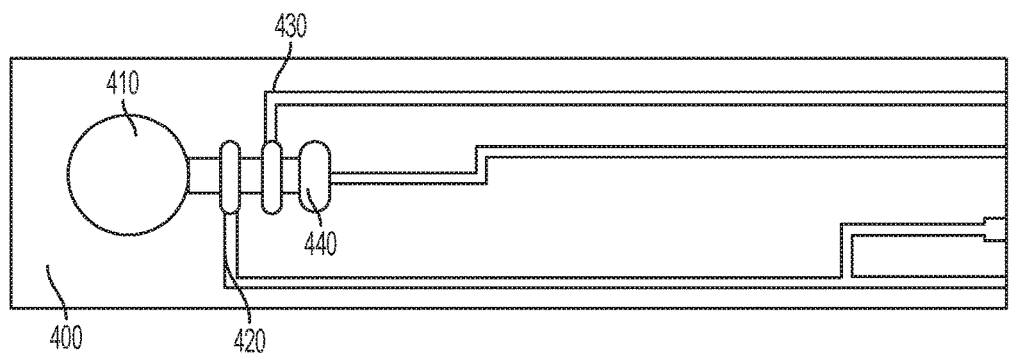
FIG. 4 shows one embodiment of an electrochemical test strip for receiving a sample from the sampler of FIGS. 3a-3c.

FIG. 4 shows one embodiment of an electrochemical test strip for receiving a sample from the sampler of FIGS. 3a-3c. In this strip 400, a receiving port 410 is provided for receiving a sample from the sampler. A fill detection electrode 420 may be provided. Additionally, an electrode 430 and counter electrode 440 are provided.

In addition to having a single electrochemical ALT or AST sensor, in some embodiments, a versatile electrochemical test strip and offer multiple tests on the same strip. The figures below show an embodiment with multiple blood application sites. However, this in some embodiments, the system has a single blood application site.

Figure 5:
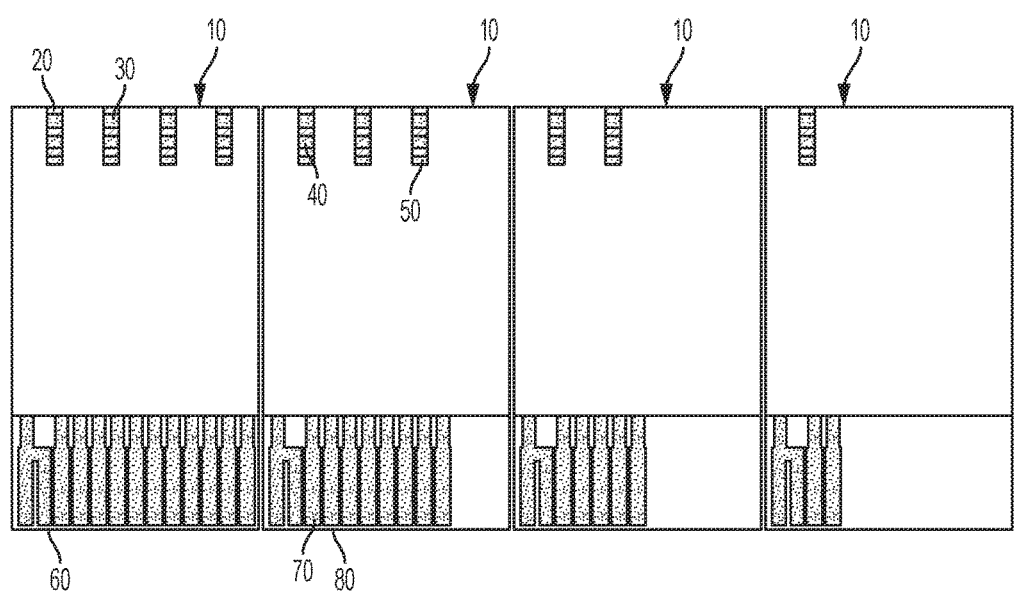
FIG. 5 shows that ALT and AST tests can be combined as a joint test strip and shows one embodiment of such a strip.
Figure 6:
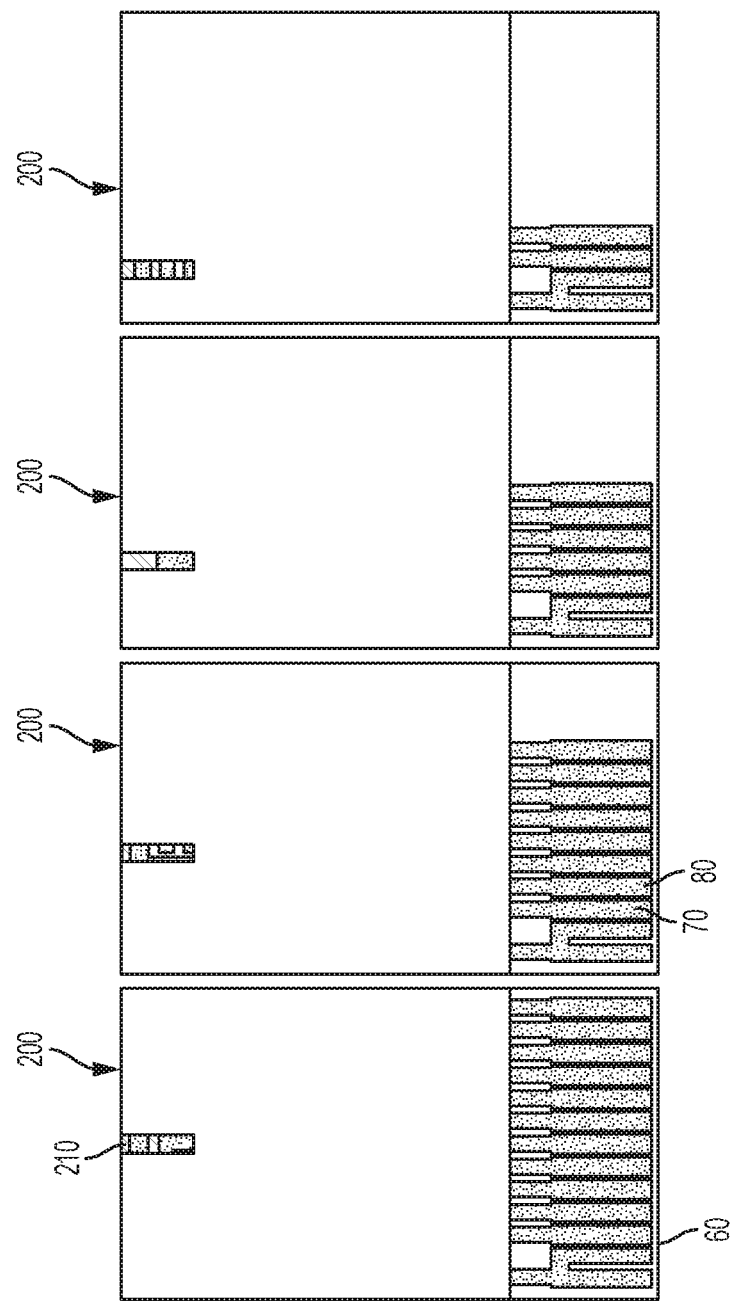
FIG. 6 shows an embodiment with a single sampling port.
Figure 7:
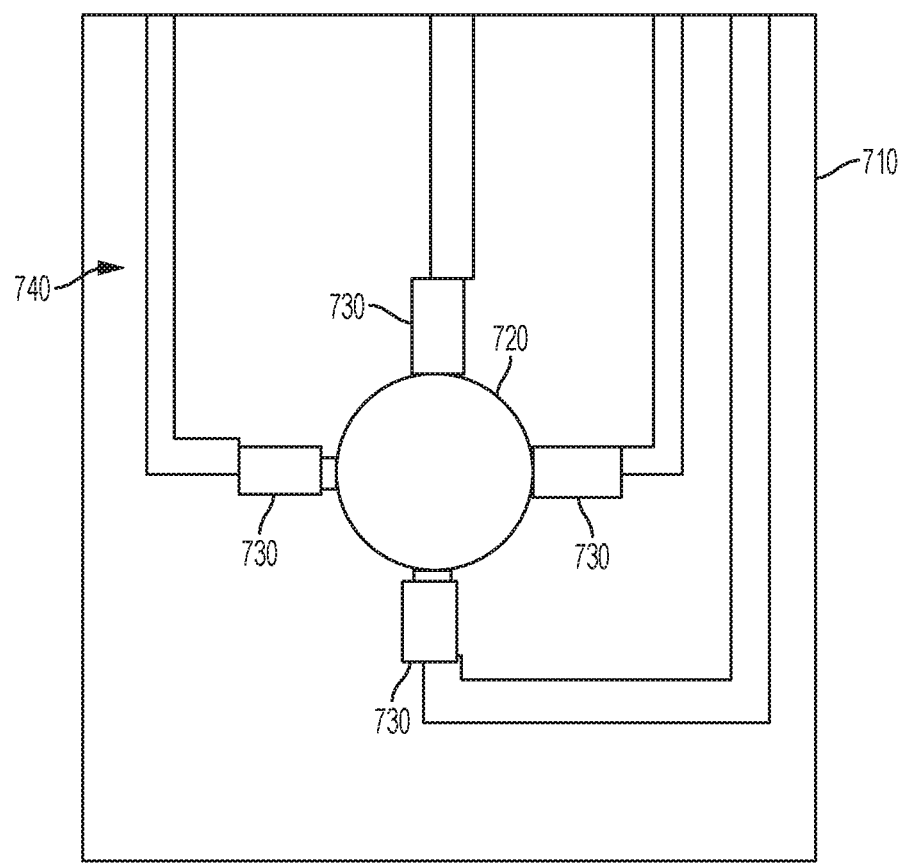
FIG. 7 shows an embodiment of strip with a receiving port for a sampler.

FIG. 5 shows that ALT and AST tests can be combined as a joint test. In addition, other tests may be combined with ALT and AST such as glucose and ketones. FIG. 5 shows one embodiment of the strip design. Shown are four strips 10. From left to right, the strips 10 have 4, 3, 2, and 1 sample receiving ports 20. Each sample receiving port may have an electrode 30, a counter electrode 40, and a reference electrode 50. The reference electrode 50 may provide for a fill indication, as it will only pass a voltage when the sample reaches the electrode 50. The contacts 70, 80 are also visible, which interconnect with the electrodes and connect to contacts in the meter when inserted. The strip size does not change depending on the number of assays. FIG. 5 displays a separate blood sampling port for each assay. Some embodiments may include separate sampling ports, particularly if there could be "cross talk" between reagents. FIG. 6 shows an embodiment with a single sampling port. In many embodiments, there will be a singular sampling port 210 for the multi-analyte panels. Again, this strip allows for adaptability of design to meet the needs of particular assays. As shown in the left-most strip, a single sample port 210 may provide for five different sets of contacts, providing for the testing of five different analyte tests. Various combinations of analytes may be used in the strips as described herein. In some embodiments, a central application point is available for the sampler. This eases the challenge of dosing a large number of ports. As shown in FIG. 7, a possible geometry for such a configuration is shown. Test strip 710 includes a receiving port 720, similar to receiving port 410 of FIG. 4. The receiving port 720 is sized in a complementary fashion to that of a sampler that may include a premix set. The receiving port 720 includes tubes 730 (typically capillary tubes) for extracting a portion of the sample. Also shown are the contact wires 740, the connect to the electrodes that are typically located in the tubes 730. The arrangement shown is only one possible arrangement for a receiving port with multiple interconnected capillary channels. A large number of geometries are possible. Additionally, in some embodiments, the receiving port 720 may include a first and second set point. When the sampler is inserted and pushed to the first set point in the receiving port 720, the sample may be distributed to the tubes 730. After distribution, the sampler may be further advanced to separate the sampler from the sample contained in the tubes 730. In such a scenario receiving port may include breakaway tabs at the first set point through which the user may push the sampler, in order to reach the second set point, whereby fluidic communication between the sample in the tubes is lessened. This may decrease cross talk.

The pyruvate reaction pathway may apply to the detection of other analytes as well. For instance, in one embodiment, this phosphate may react in a similar fashion. The pyruvate reaction where pyruvate oxidase from *E. Coli* reacts with the mediator for an electrochemical ALT and AST assay (see reaction below) can be used for an electrochemical detection scheme.

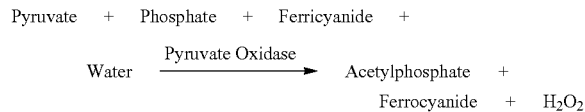

Therefore, it is also possible to have an electrochemical phosphate assay. By providing the pyruvate, ferricyanide, and pyruvate oxidase, one can easily develop an electrochemical phosphate assay. A phosphate assay would be an excellent companion assay with a Vitamin D test. It also could be used in a non-medical application in water testing. One challenge is that many pyruvate oxidase enzymes have been lyophilized from a phosphate buffer. A pyruvate oxidase enzyme that is not provided in a phosphate buffer is needed in some embodiments to complete this assay.

In conclusion, embodiments for an electrochemical ALT, AST, and phosphate sensor are provided herein. An electrochemical point-of-care ALT/AST test does not previously exist. The ALT and AST tests could be beneficial to those taking medications which could possibly impair liver function. It also may be used in small clinics to determine levels of ALT or AST for further medical diagnosis. Furthermore, having an electrochemical phosphate assay could be used as a companion diagnostic to a Vitamin D assay or a stand-alone test.

While specific embodiments have been described in detail in the foregoing detailed description and illustrated in the accompanying drawings, it will be appreciated by those skilled in the art that various modifications and alternatives to those details could be developed in light of the overall teachings of the disclosure and the broad inventive concepts thereof. It is understood, therefore, that the scope of this disclosure is not limited to the particular examples and implementations disclosed herein but is intended to cover modifications within the spirit and scope thereof as defined by the appended claims and any and all equivalents thereof.

What is claimed as new and desired to be protected by Letters Patent of the United States is:

1. A system for electrochemically detecting AST and ALT, the system comprising:
    a first sampler containing L-Alanine+alpha-Ketoglutarate, said first sampler receiving a first blood sample and producing pyruvate from ALT in the first blood sample;
    a second sampler containing L-Aspartic acid+alpha-Ketoglutarate, said second sampler receiving a second blood sample and producing pyruvate from AST in the second blood sample;
    at least one electrochemical test strip containing, pyruvate oxidase from *E. coli*, phosphate and ferricyanide receiving the first and second blood samples from the first and second samplers; and
    a meter reading the at least one electrochemical test strip and indicating a amount of ALT and AST in the first and second blood samples.

2. The system of claim 1, wherein the second sampler further contains oxaloacetate decarboxylase.

3. The system of claim 1 in which said at least one electrochemical test strip further contains oxaloacetate decarboxylase.

4. The system of claim 1 in which said meter uses amperometry or reading the at least one electrochemical test strip.

5. The system of claim 1 which comprises a first electrochemical test strip and a second electrochemical test strip, the first electrochemical test strip receiving the first blood sample from the first sampler and the second electrochemical test strip receiving the second blood sample from the second sampler, said meter reading the first electrochemical test strip and indicating an amount of ALT in the first blood sample, said meter reading the second electrochemical test strip and indicating an amount of AST in the second blood sample.

* * * * *